(12) United States Patent
Namdeo et al.

(10) Patent No.: US 9,095,514 B2
(45) Date of Patent: Aug. 4, 2015

(54) PHARMACEUTICAL COMPOSITION

(75) Inventors: Alok B. Namdeo, Baroda (IN); Narayanaswamy Subramanian, Baroda (IN); Subhas Balaram Bhowmick, Baroda (IN)

(73) Assignee: SUN PHARMA ADVANCED RESEARCH COMPANY LTD., Mumbai (IN)

( * ) Notice: Subject to any disclaimer, the term of this patent is extended or adjusted under 35 U.S.C. 154(b) by 95 days.

(21) Appl. No.: 13/143,808

(22) PCT Filed: Jan. 8, 2010

(86) PCT No.: PCT/IN2010/000015
§ 371 (c)(1),
(2), (4) Date: Jul. 8, 2011

(87) PCT Pub. No.: WO2010/089768
PCT Pub. Date: Aug. 12, 2010

(65) Prior Publication Data
US 2011/0275597 A1    Nov. 10, 2011

(30) Foreign Application Priority Data
Jan. 9, 2009  (IN) .............................. 58/MUM/2009

(51) Int. Cl.
| A61K 9/19 | (2006.01) |
| A61K 9/00 | (2006.01) |
| A61K 31/133 | (2006.01) |
| A61K 31/69 | (2006.01) |
| A61K 45/06 | (2006.01) |

(52) U.S. Cl.
CPC ................. *A61K 9/19* (2013.01); *A61K 9/0019* (2013.01); *A61K 31/133* (2013.01); *A61K 31/69* (2013.01); *A61K 45/06* (2013.01)

(58) Field of Classification Search
CPC ........................................................ A61K 9/19
See application file for complete search history.

(56) References Cited

U.S. PATENT DOCUMENTS

| 6,617,317 B1 | 9/2003 | Adams et al. | |
| 6,713,446 B2 * | 3/2004 | Gupta | ............................ 514/1.1 |
| 2006/0084592 A1 | 4/2006 | Boucher | |

FOREIGN PATENT DOCUMENTS

WO    2009-026427 A2    2/2009

OTHER PUBLICATIONS extemp.ie, http://www.extemp.ie/pdfs/sterile_preperations.pdf. accessed Feb. 2013.*
Velcade(R) product insert. Jul. 2008.*
André P, Cisternino S, Chiadmi F, Toledano A, Schlatter J, Fain O, Fontan JE. Stability of bortezomib 1-mg/mL solution in plastic syringe and glass vial. Ann Pharmacother. Sep. 2005;39(9):1462-6. Epub Jun. 28, 2005.(abstract only provided).*
International Search Report for PCT/IN2010/000015, mailing date of Sep. 7, 2010.

* cited by examiner

*Primary Examiner* — Paul Zarek
(74) *Attorney, Agent, or Firm* — Sughrue Mion, PLLC

(57) ABSTRACT

The present invention relates to a parenteral pharmaceutical composition comprising therapeutically effective amounts of N-(2-pyrazine)carbonyl-L-phenylalanine-L-leucine boronic acid or its salts or its derivatives and tromethamine wherein the composition is stable.

3 Claims, 2 Drawing Sheets

PHARMACEUTICAL COMPOSITION

Figure 1:
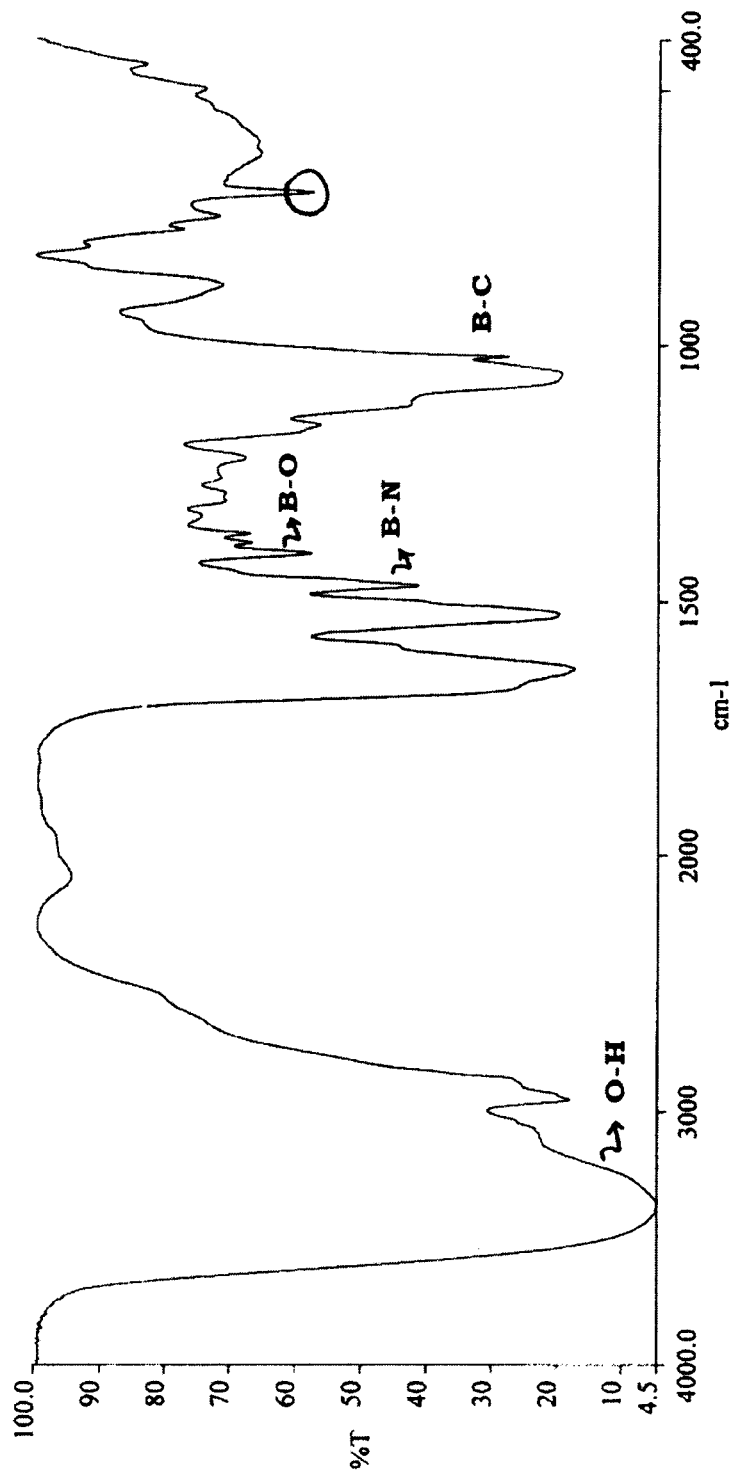

The present invention relates to a novel parenteral pharmaceutical composition comprising N-(2-pyrazine) carbonyl-L-phenylalanine-L-leucine boronic acid and tromethamine. Such composition in lyophilized dry form is stable at room temperature and upon reconstitution forms aqueous solutions that are stable for at least 12 hours.

BACKGROUND OF THE INVENTION

Bortezomib is N-(2-pyrazine) carbonyl-L-phenylalanine-L-leucine boronic acid.

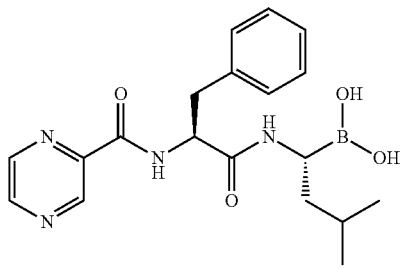 [SMILES: CC(C)C[C@H](NC(=O)[C@H](Cc1ccccc1)NC(=O)c1cnccn1)B(O)O]

Solid bortezomib is not soluble at a concentration of 1 mg/ml in 0.9% w/v of sodium chloride. It is commercially available under the trade name of Velcade® for injection. It is given intravenously only and contains mannitol ester of bortezomib. It is available in a lyophilized form which when reconstituted forms a solution consisting of the mannitol ester in equilibrium with bortezomib. Velcade® is reconstituted with 0.9% sodium chloride to a final concentration of 1 mg/ml of bortezomib. The use of mannitol provides the desired solubility. The prescribing information (*Physician Desk Reference*, published by Thomson Healthcare, 62 *edition,* 2008, pp. 2151-2157) provides that the reconstituted product should be clear and colorless and should be visually inspected for particulate matter and discoloration and only clear solution which is not discolored should be used within eight hours after preparation. This guidance is in view of the extreme precautions required in administering drugs directly into the intravenous system. Formation of particles is undesirable and preparations should meet high purity requirements.

U.S. Pat. No. 6,713,446 describes that bortezomib is known to be stable for more than 2 years when stored at $-2°$ C. to $-20°$ C., as determined by HPLC analysis (purity>97%). But when stored at 2° C.-8° C., the product is not stable for longer than 3-6 months. U.S. Pat. No. 6,713,446 (hereinafter referred to '446) provides a stable, pharmaceutically acceptable composition comprising bortezomib. The claims of the patent encompass the commercially available Velcade® for injection. The inventors of the '446 patent have discovered that lyophilization of an aqueous mixture comprising a boronic acid compound and a compound having at least two hydroxyl groups provides a stable composition. The lyophilized material was readily soluble at concentration up to 6 mg/ml.

U.S. Pat. No. 6,617,317 (hereinafter referred to as patent '317) discloses a method for reducing the rate of degradation of proteins in an animal comprising contacting cells of the animal with certain boronic ester and acid compounds. Also disclosed are novel boronic ester and acid compounds, their synthesis and uses. The patent further discloses that the novel boronic ester and acid compounds can be converted to their basic salts by mixing a solution of a boronic acid ($Z^1$ and $Z^2$ are both OH) of the invention with a solution of a pharmaceutically acceptable non-toxic base, such as, sodium hydroxide, potassium hydroxide, sodium bicarbonate, sodium carbonate, or an amino compound, such as choline hydroxide, Tris, bis-Tris, N-methylglucamine or arginine. Water-soluble salts are preferable. The suitable salts that have been listed include: alkaline metal salts (sodium, potassium etc.), alkaline earth metal salts (magnesium, calcium etc.), ammonium salts and salts of pharmaceutically acceptable amines (tetramethylammonium, triethylamine, methylamine, dimethylamine, cyclopentylamine, benzylamine, phenethylamine, piperidine monoethanolamine, diethanolamine, tris(hydroxymethyl)amine, lysine, arginine and N-methyl-D-glucamine).

The chemical stability and stability problem of the parenteral formulation of Bortezomib has been reported in Sara Wu et al *J. Pharm. Sci* 89; 758-765, 2000 pp. 759-765). The reference indicates that the bortezomib showed erratic behaviour and was quite unstable in certain solvents. The authors also reported some observations on the effect of ascorbic acid and EDTA on its stability. Under acidic and basic conditions, it was observed that impurity D—an oxidative impurity was a major degradant. The article mentions that the degradation and pre-formulation studies of bortezomib was found to be quite complicated.

In attempts to prepare stable parenteral composition of bortezomib, the inventors of the present invention prepared solutions using various solubilizing agents. At a concentration of 1 mg bortezomib per ml, clear solution was obtained with certain solubilizing agents. Although a clear solution was obtained, it was observed that particles were rapidly formed in such solutions. In instances where the inventors had success in preventing particle formation, it was found that when the solutions were lyophilized, the lyophilized preparation was difficult to reconstitute into a ready clear aqueous solution. The inventors of the present invention have surprisingly discovered that these problems are resolved by preparing a composition comprising bortezomib and tromethamine with the pH adjusted in the range of 6.8 to 8.4. The inventors also identified that the problems of instability of the pharmaceutical composition in dry form as well as in a reconstituted form was connected to the impurity levels present in the bulk of the bortezomib. For instance, when bortezomib bulk with total impurity levels of about 3%, was used for preparing the injectable composition, the pH when adjusted to 7.6-8.4, the composition remained stable for desired period whereas when the bulk of bortezomib having total impurity levels less than 0.51% was utilized, the pH of the composition when adjusted to a pH of about 6.8-8.2, the composition remained stable for desired period.

SUMMARY OF THE INVENTION

The present invention provides a parenteral pharmaceutical composition comprising therapeutically effective amount of N-(2-pyrazine) carbonyl-L-phenylalanine-L-leucine boronic acid or its salts or its derivative and tromethamine wherein the composition is stable.

The present invention also provides a method for formulating a therapeutically effective amount of N-(2-pyrazine) carbonyl-L-phenylalanine-L-leucine boronic acid or its salts or its derivatives, said the method comprising steps of:

(a) preparing an aqueous mixture comprising
   (i) N-(2-pyrazine) carbonyl-L-phenylalanine-L-leucine boronic acid or its salts or its derivatives,
   (ii) tromethamine and a optionally a bulking agent and
(b) adjusting the pH of the solution to a pH of about 6.8 to 8.2 and
(c) lyophilizing the solution of (b).

The present invention particularly, provides a pharmaceutical composition comprising therapeutically effective amounts of bortezomib or its salt or its derivatives and tromethamine wherein the pH of the said composition is in the range of 6.8 to 8.4, preferably 7.0 to 8.2.

The present invention still further provides a lyophilized pharmaceutical composition comprising therapeutically effective amounts of bortezomib and tromethamine wherein the pH of the said composition is in the range of 6.8 to 8.4, preferably 7.0 to 8.2.

DESCRIPTION OF THE DRAWINGS AND FIGURES

Figure 2:
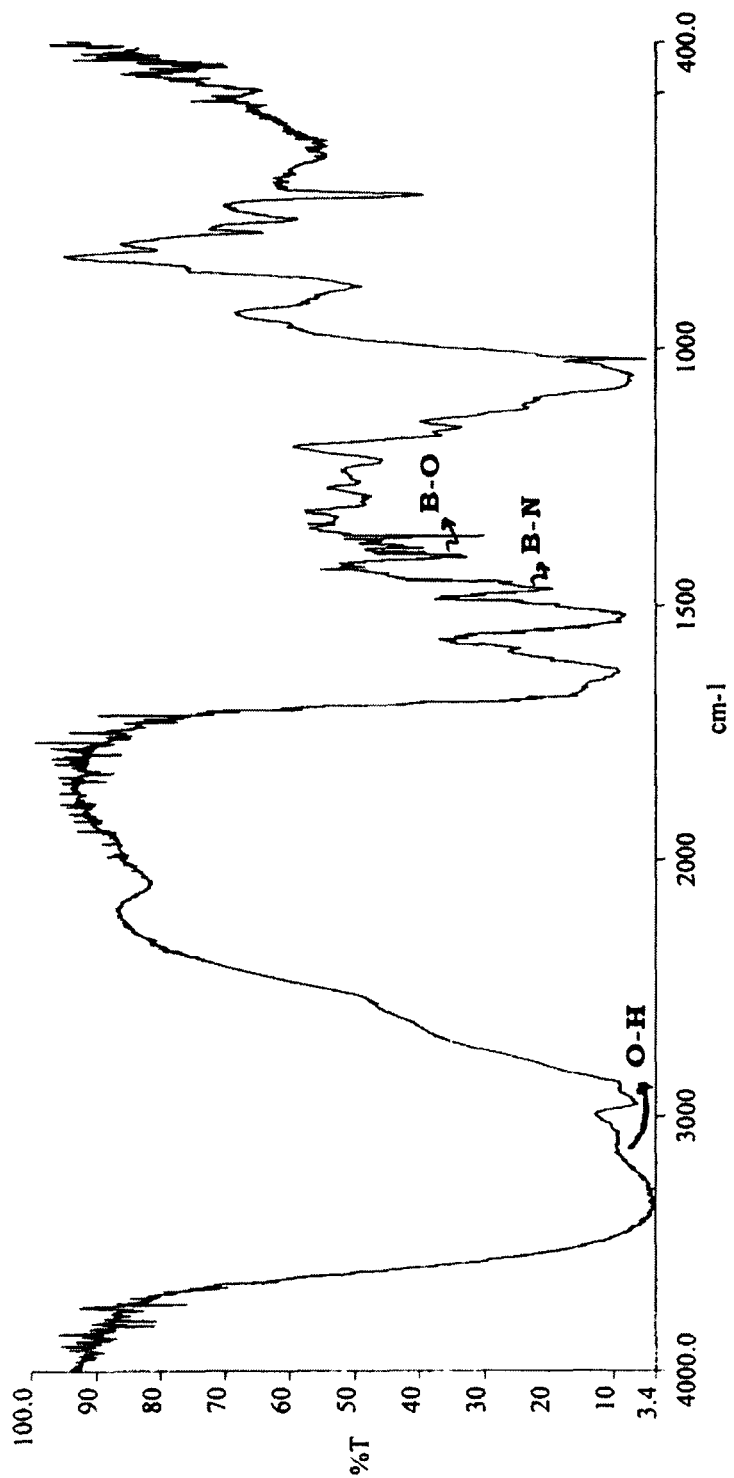

The IR spectrum of the lyophilized composition according to Example 1 and Example 2 of the present invention were recorded and is given in FIG. 1 and FIG. 2, respectively.

DETAILED DESCRIPTION OF THE INVENTION

The term "lyophilized composition" as used herein refers to any solid material obtained by lyophilization or freeze drying of an aqueous mixture. It may be also referred to as freeze dried mass.

By "stable composition" is meant any composition having sufficient stability to have utility as a pharmaceutical agent. Preferably, the formulation has sufficient stability to allow storage at a convenient temperature, preferably between 0° C. and 40° C., for a reasonable period of time, preferably longer than one month, more preferably longer than three months, even more preferably longer than six months, and most preferably longer than one year. Also, the term 'stable composition' as used herein means that the pharmaceutical composition when in the form of a lyophilized cake or powder that is the composition is not reconstituted, remains unaltered in terms of physical and chemical parameters for a prolonged period of time when packed in container which are either protected or unprotected against light, under various storage conditions. For instance, when the containers such as vials are not opened and are stored at controlled room temperature 25° C. (77° F.) with variation to a range of about 15 to 30° C. (59° F. to 86° F.) the pharmaceutical composition of the present invention remains stable for 6 months. The pharmaceutical composition when reconstituted with a suitable reconstitution medium such as water for injection, the reconstituted solution is said to be stable when there is no significant chemical degradation for at least 12 hours, preferably 24 hours and there are no signs of precipitation or appearance of particles in the clear solution on storage at room temperature for the said time.

In one embodiment of the present invention, the parenteral pharmaceutical composition upon reconstitution remains stable for at least 12 hours, preferably 24 hours and the total impurities in the clear solution are found to be less than 0.68 at 1 month when stored at 40° C. and 75% relative humidity.

In preferred embodiments, the pharmaceutical composition of the present invention is free of any added preservatives. It was surprisingly found that the composition in either dry form or after reconstitution, in-spite of being preservative free, the composition remained stable for longer period of time i.e if in the dry form, the composition remained stable for 6 months at ambient temperature or if reconstituted with a suitable reconstitution media, for at least 24 hours, preferably 12 hours. It is very important that the reconstituted composition remains physically and chemically stable during the period of administration. Usually, this reconstituted composition may be administered to the patients along with other active ingredients either intravenously or by oral administration. Generally, the reconstituted composition of the present invention is administered as a bolus intravenous injection. Sometimes, it may be required to monitor the complete blood count (CBC) during the administration of the parenteral composition. The present invention provides a stable pharmaceutical composition comprising therapeutically effective amounts of N-(2-pyrazine) carbonyl-L-phenylalanine-L-leucine boronic acid or its salts or its derivatives and tromethamine wherein the pH of the said composition is in the range of 6.8 to 8.4, preferably 7.0 to 8.2.

The present invention provides a lyophilized pharmaceutical composition comprising therapeutically effective amount of N-(2-pyrazine) carbonyl-L-phenylalanine-L-leucine boronic acid or its salts or its derivatives and tromethamine wherein the pH of the said composition is in the range of 6.8 to 8.4, preferably 7.0 to 8.2.

The present invention also provides a pharmaceutical composition comprising therapeutically effective amounts of N-(2-pyrazine) carbonyl-L-phenylalanine-L-leucine boronic acid or its salts or its derivatives and tromethamine wherein the pH of the composition is in the range of 7.6 to 8.4, preferably 7.9 to 8.1.

In one embodiment, the present invention provides a lyophilized pharmaceutical composition comprising therapeutically effective amounts of N-(2-pyrazine) carbonyl-L-phenylalanine-L-leucine boronic acid or its salts or its derivatives and tromethamine wherein the pH of the composition is in the range of 7.6 to 8.4, preferably 7.9 to 8.1.

The inventors further identified that the stability problems and the solution to this problem is associated with the source of the bortezomib that is employed in the preparation of the parenteral pharmaceutical composition of the present invention. For instance, when one source of bortezomib was used for preparing the injectable composition, when its pH was adjusted to 7.6-8.4, the composition remained stable for desired period whereas when another source of the bulk of bortezomib was utilized, the pH of the composition was adjusted to a pH of about 6.8-8.2, the composition remained stable for desired period. Therefore, not only the active pharmaceutical ingredient, but the type and amount of the impurities present in it, seemed to play a role in the achieving the stability of the dry as well as reconstituted composition.

The bortezomib bulk (API) used in the present invention can be synthesized by various synthetic ways. In one embodiment, the inventors found that when the bortezomib having a specific optical rotation of about −53.4°, residual solvent content of less than 100 ppm and total impurities less than 0.51% and known identified impurity such as impurity B were less than about 0.1% and impurity H were is less than about 0.04% and any single maximum unknown impurity was less than 0.11%, an injectable composition comprising such a source of bortezomib could be prepared by adjusting the pH of the solution in the range of about 7.0 to about 7.5. However, when bortezomib of any other grade which does not satisfy these limits of impurities was employed, it was found that a stable injectable composition could be prepared by adjusting the pH in the range of about 7.9 to about 8.4.

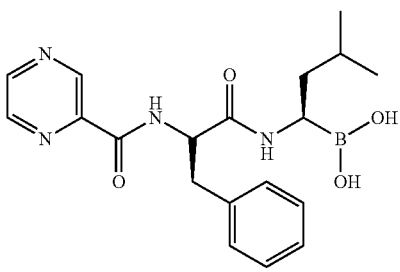

Impurity A: chiral isomer: [(1R)-3-methyl-1-[[(2S)-1-oxo-3-phenyl-2-[(pyrazinylcarbonyl)amino]propyl]amino]butyl]boronic acid

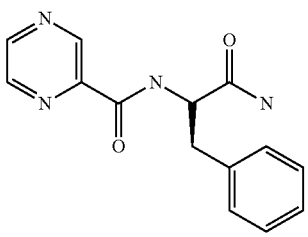

Impurity H: 3-phenyl-2-[(pyrazine-2-carbomy)amino]-propionionamide

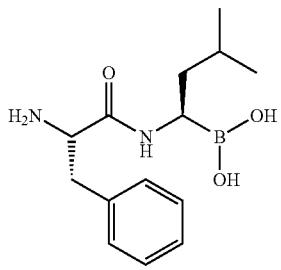

Impurity B: L-phenylalanine-L-leucine boronic acid

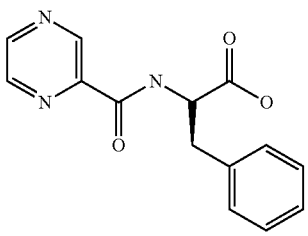

Impurity I:
3-phenyl-2-[(pyrazine-2-carbomyl)amino]-propionic acid

The pharmaceutical composition comprises therapeutically effective amounts of N-(2-pyrazine) carbonyl-L-phenylalanine-L-leucine boronic acid or its salts or its derivatives.

The amount of bortezomib in the pharmaceutical composition of the present invention ranges from about 0.1 mg/ml to about 5 mg/ml, preferably about 0.5 mg/ml to about 2 mg/ml and most preferably, about 1 mg/ml.

The pharmaceutical composition comprises tromethamine which is chemically known as 2-amino-2-(hydroxymethyl) propane-1,3-diol. Particularly, a parenteral grade or a USP complying grade of tromethamine is suitable for the pharmaceutical composition. The amount of tromethamine in the pharmaceutical composition of the present invention ranges from about 0.1 mg/ml to about 5 mg/ml, preferably about 0.5 mg/ml to about 2 mg/ml and most preferably, about 1 mg/ml. It was observed that for one mole of bortezomib about 3 moles of tromethamine gave satisfactory solubility to bortezomib.

In one embodiment of the present invention, apart from tromethamine and water for injection, the solution may additionally comprise of acid, such as for example, hydrochloric acid to adjust to pH of the composition to a desirable range. It is critical that the pH of the solution is adjusted in the range of 7.6 to 8.4. It was found that when the pH of the composition was adjusted beyond the specified range, there was presence of particles indicating precipitation of bortezomib and/or there was difficulty on the reconstitution of the lyophilized cake. Quick and complete reconstitution of the lyophilized cake was found when the pH of the composition was adjusted in the range of 6.8 to 8.2, preferably in the range of 7.0 to 8.1. The IR spectrum of the lyophilized composition according to Example 1 and Example 2 of the present invention were recorded and is given in FIG. 1 and FIG. 2. The IR spectroscopy of the composition shows a strong B—N bond indicating formation of tromethamine salt of bortezomib. It may be said without wishing to be bound by any theory, that the completion of salt formation may be important in the quicker reconstitution of the lyophilized cake. The preferred pharmaceutical composition may be readily reconstituted in about 30 seconds. By the term readily means without the application of any external energy such as sonication. Simple swirling or movement of the container in which the composition is stored for reconstituting the cake or powdery mass is also meant to be readily reconstituted.

Additionally, the composition may include, tonicity adjusting agents, bulking agents and the like and mixtures thereof. Examples of tonicity adjusting agents include, but are not limited to, sodium chloride, mannitol, lactose, sucrose, maltose, trehalose and the like and mixtures thereof. In one embodiment, sodium chloride is used as a tonicity adjusting agent and/or bulking agent. The amount of sodium chloride that may be used in the pharmaceutical composition of the present invention includes, but is not limited to, 0 mg to about 100 mg per ml of the solution, preferably about 15 mg to 45 mg of the solution. Any other suitable tonicity agent such as sugar, sugar alcohols may also be employed.

In one embodiment, the present invention provides a lyophilized pharmaceutical composition comprising therapeutically effective amounts of bortezomib wherein the source of bortezomib used has total impurities of about 2.5% and tromethamine, wherein the pH of the composition is in the range of 7.6 to 8.4, preferably 7.9 to 8.1.

In another embodiment, the present invention provides lyophilized pharmaceutical composition comprising therapeutically effective amounts of bortezomib wherein the bortezomib source used has total impurities of about 0.5% and tromethamine, wherein the pH of the composition is in the range of 6.8 to 8.4, preferably 7.0 to 8.1.

In an embodiment, when the composition of the present invention is in a lyophilized form, a bulking agent may be added in the composition. As used herein, the term "bulking agent" is intended to mean a compound used to add bulk to the lyophilized product and/or assist in the control of the properties of the formulation during lyophilization. Examples of bulking agents that may be used include, but are not limited to, dextran, trehalose, sucrose, polyvinylpyrrolidone, sodium chloride, lactose, inositol, sorbitol, albumin, calcium lactobionate and others known to those of ordinary skill in the art.

When the pharmaceutical composition is in the form of a lyophilized product, the composition may include apart from tonicity adjusting agents, bulking agent, cryoprotectants. The term 'cryoprotectant' used is intended to mean a compound used to protect an active therapeutic agent from physical or chemical degradation during lyophilization. Examples of cryoprotectants that may be used include, but are not limited to, carbohydrates such as monosaccharides, disaccharides and sugar alcohols. Examples of the carbohydrates that may be used include, but are not limited to, mannitol, sucrose and others known to those of ordinary skill in the art.

The pharmaceutical composition of the present invention may be prepared by simply mixing the required amounts of N-(2-pyrazine) carbonyl-L-phenylalanine-L-leucine boronic acid and tromethamine and adding water for injection with continuous stirring. The solution may be warmed at 45° C. to 50° C. to form a clear solution. The solution may then be filtered through 0.2 to 0.8 micron syringe filter, preferably 0.45 micron filter and then the pH is determined. The pH of the clear solution is further adjusted with hydrochloric acid in the range of 7.6 to 8.4, preferably in the range of 7.9 to 8.1.

According to one embodiment, the pH adjusted clear solution may be subjected to lyophilization or freeze drying.

Generally, the lyophilization involves two steps namely, thermal treatment step wherein no vacuum is applied and the actual primary drying step wherein vacuum is applied. The solution subjected to lyophilization is filled into vials with specialized stoppers. The vials filled with the solution to be dried are placed in the lyophilizer. In the thermal treatment step, temperature of shelf of lyophilizer where the vials of solution filled is stored, is gradually decreased from 20° C. to −40° C. Then the frozen solution is subjected to drying step. For example, in this instance, the temperature is set from −40° C. to −15° C. for the time cycle of about 5 to 6 hours at a vacuum of about 100 to 200 mTorr. At this time and temperature, the ice is dried. Then the temperature of the material is raised to +10° C. to about +25° C. at a vacuum of about 50 mTorr in which the residual solvent if any is removed. The lyophilized composition or commonly referred to as lyophilized cake in the vials may then be subjected to reconstitution at the time of administration.

It was found that the reconstitution of the lyophilized cake of the pharmaceutical composition of the present invention takes less than 90 seconds without any need of bath-sonication. Also, the reconstituted solution was found to be stable in terms of particle formation for at least 12 hours i.e no particulates were observed and also was chemically stable.

It will be understood by those of skill in the art that numerous modifications can be made without departing from the spirit of the present invention. Therefore, it should be clearly understood that the following examples are illustrative only and should not to be construed to limit the scope of the present invention.

TABLE 1

Comparative examples I-IX

| Comparative Example | Ingredients per vial | Observation | conclusion |
|---|---|---|---|
| I | Bortezomib (1 mg) + polysorbate (100 mg) The solution was stirred at 50 to 60° C., water for injection quantity sufficient to 0.5 ml | Solution was stored at RT Precipitation was observed within 2 hours | Not soluble in polysorbate 80 |
| II | Bortezomib (1 mg) + polysorbate (100 mg), water for injection quantity sufficient to 1 ml - sonication applied | Fibrous particles observed | Not soluble in polysorbate 80 |
| III | Bortezomib (1 mg) + ethanol (0.1 ml) + polysorbate (100 mg) water for injection quantity sufficient to 1 ml | Fibrous particles observed when stored at 20° C.-8° C. | Not soluble in polysorbate 80 and ethanol |
| IV | Bortezomib (1 mg) + polyethylene glycol 400 (600 mg), water for injection quantity sufficient to 5 ml | Clear solution initially but fibrous particles observed on storage | Not soluble on storage |
| V | Bortezomib (5 mg) + polyethylene glycol 400 (600 mg) + polysorbate 80 water for injection quantity sufficient to 5 ml | Hazy solution particles observed on storage at RT after 2 hours | Not soluble on storage |
| VI | Bortezomib (3.5 mg) + n-butanol 0.3 ml, 30 mg sodium chloride water for injection sufficient to 0.7 ml | Bortezomib solubilizers in 30% t-butanol, after reconstitution with water for injection, particles observed | Not soluble on storage |
| VII | Bortezomib (3.5 mg) + n-butanol 0.4 ml + L-Cysteine hydrochloride hydrate 4.78 mg + sodium chloride 30 mg, water for injection sufficient to 0.6 ml - final solution filtered using 0.45 micron filter and lyophilized | Clear solution on bath sonication Reconstitution of lyophilized cake takes more than 2 minutes | Reconstitution of cake not easy and takes long time |
| VIII | Bortezomib (3.5 mg) + polyethylene glycol 400 (420 mg) + hydroxypropyl beta cyclodextrin 175 mg, water for injection sufficient to make 3.5 ml | Particulate matter observed | Drug not solubilized |
| IX | Bortezomib (3.5 mg) + sodium hydroxide (2.4 mg) + L-Cysteine Hydrochloride•hydrate (478 mg) + sodium chloride (2.4 mg) water for injection sufficient to make 1.0 ml - final solution filtered using 0.45 micron filter and lyophilized | Clear solution was obtained Reconstitution of lyophilized cake took long time (more than 2 minutes) | Reconstitution of cake not easy and takes long time |

Comparative Example X

Bortezomib (3.5 mg) having total impurity of about 2.75% with substantial residual solvent content was used. The bulk of the bortezomib was accurately weighed and taken in a 5 ml vial. Tromethamine (3.31 mg) was weighed and mixed in the vial. Water for injection (quantity sufficient to make 1 ml) was added with continuous stirring. The solution was warmed at 45° C. to 50° C. to form a clear solution. The solution was cooled and 30 mg of sodium chloride was added to the cooled solution. The solution was filtered through 0.45 micron syringe filter and the pH was determined. The pH of the clear solution was found to be 8.51. The clear solution was lyophilized. The solid mass when subjected to reconstitution it was found that it took more than 120 seconds. A bath sonication was required to break the lyophilized cake to get a solution. After reconstitution, the solution was found to be stable in terms of particle formation for 24 hours.

Comparative Example XI

Bortezomib (3.5 mg) having total impurity of about 2.75% was used in this composition. The bulk of bortezomib was accurately weighed and taken in a 5 ml vial. Tromethamine (3.31 mg) was weighed and mixed in the vial. Water for injection (quantity sufficient to make 1 ml) was added with continuous stirring. The solution was warmed at 45° C. to 50° C. to form a clear solution. The solution was cooled and 30 mg of sodium chloride was added to the cooled solution. The solution was filtered through 0.45 micron syringe filter and the pH was determined. The pH of the clear solution was 8.63 which was adjusted with 1% hydrochloric acid to 7.28. The clear solution was lyophilized. The reconstitution of the lyophilized cake took more than 120 seconds. After reconstitution, the solution was found to be unstable in terms of particle formation for 24 hours i.e particulates were observed.

Comparative Example X

Bortezomib (3.5 mg) having total impurity of about 2.75% was used to formulate the composition. The bortezomib was accurately weighed and taken in a 5 ml vial. Tromethamine (3.31 mg) was weighed and mixed in the vial. Water for injection (quantity sufficient to make 1 ml) was added with continuous stirring. The solution was warmed at 45° C. to 50° C. to form a clear solution. The solution was filtered through 0.45 micron syringe filter and the pH was determined. The pH of the clear solution was 8.63 which was further adjusted with 1% hydrochloric acid to 7.5. The clear solution was lyophilized. The reconstitution of the lyophilized cake took more than 120 seconds. After reconstitution, the solution was found to be unstable in terms of particle formation for 24 hours i.e particulates were observed.

Example I 3.5 mg of Bortezomib having a total impurity of about 2.75% was taken. Tromethamine (3.31 mg) was weighed and mixed in the vial. Water for injection (quantity sufficient to make 1 ml) was added with continuous stirring. The solution was warmed at 45 to 50° C. to form a clear solution. The solution was cooled and 30 mg of sodium chloride was added to the cooled solution. The solution was filtered through 0.45 micron syringe filter and the pH was determined. The pH of the clear solution was 8.68 which was adjusted with 5% hydrochloric acid to 8.01. The clear solution was lyophilized. The reconstitution of the lyophilized cake took less than 30 seconds without any need of bath sonication. After reconstitution, the solution was found to be stable in terms of particle formation for 24 hours i.e no particulates were observed. The IR spectrum of the lyophilized composition was recorded. The IR spectrum is given in FIG. 1. The IR spectroscopy of the formula indicates formation of tromethamine salt having a strong B—N bond.

Example II 3.5 mg of Bortezomib having a total impurity of about 2.75% was taken. Tromethamine (3.31 mg) was weighed total impurity less than 0.51%, with optical rotation of −53.4° and impurity A was accurately weighed and taken in a 5 ml vial. Tromethamine (3.31 mg) was weighed and mixed in the vial. Water for injection (quantity sufficient to make 1 ml) was added with continuous stirring. The solution was warmed at 45° C. to 50° C. to form a clear solution. The solution was cooled and 30 mg of sodium chloride was added to the cooled solution. The solution was filtered through 0.45 micron syringe filter and the pH was determined. The pH of the clear solution was 8.68 which was adjusted with 5% hydrochloric acid to 8.01. The clear solution was lyophilized. The reconstitution of the lyophilized cake took less than 30 seconds without any need of bath sonication. After reconstitution, the solution was found to be stable in terms of particle formation for 24 hours i.e no particulates were observed. The IR spectrum of the lyophilized composition was recorded. The IR spectrum is given in FIG. 1. The IR spectroscopy of the formula indicates formation of tromethamine salt having a strong B—N bond.

Example III 3.5 mg of Bortezomib having a total impurity of about 2.75% was taken. Bortezomib (3.5 mg) was accurately weighed and taken in a 5 ml vial. Tromethamine (3.31 mg) was weighed and mixed in the vial. Water for injection (quantity sufficient to make 1 ml) was added with continuous stirring. The solution was warmed at 45° C. to 50° C. to form a clear solution. The solution was filtered through 0.45 micron syringe filter and the pH was determined. The pH of the clear solution was 8.75 which was adjusted with 5% hydrochloric acid to 7.89. The clear solution was lyophilized. The reconstitution of the lyophilized cake took less than 30 seconds without any need of bath sonication. After reconstitution, the solution was found to be stable in terms of particle formation for 24 hours i.e no particulates were observed. The IR spectrum of the lyophilized composition was recorded. The IR spectrum is given in FIG. 2. The IR spectroscopy of the formula indicates formation of tromethamine salt having a strong B—N bond.

Example IV 3.5 mg of Bortezomib having a total impurity of about 0.51%, single maximum unknown impurity of about 0.11%, specific optical rotation of about −53.4°, residual solvent content of less than 100 ppm was taken in a 5 ml vial. Tromethamine (3.31 mg) was weighed and mixed in the vial. Water for injection was added with continuous stirring. The mixture was warmed at 35° C. to 40° C. The mixture was stirred and subjected to bath sonication till clear solution was obtained. Accurately weighed quantity of sodium chloride (30 mg) was added in the vial and dissolved in the solution. The pH of the clear solution was adjusted with 5% hydrochloric acid to 8.0. The volume was made up and then the solution was filtered through 0.2-0.8 micron syringe filter. The clear solution was lyophilized in the vials. The lyophilized cake was stored in vials at various stability conditions and was subjected to the chemical and physical stability.

The results of the stability are tabulated below.

TABLE 2

Chemical stability of the lyophilized cake of composition of example IV

| Stability condition | | Water | | known and unknown impurities | | | | | | |
|---|---|---|---|---|---|---|---|---|---|---|
| Temp/humidity | Time in months | content by KF | Assay | A | B | D | H | I | $ | $$ |
| Initial | | 1.17 | 103.5 | 0.04 | ND | ND | 0.78 | 0.06 | 0.49 | 2.05 |
| 2° C.-8° C. | 1 | 0.93 | 105.4 | 0.03 | ND | ND | 0.24 | 0.02 | 0.25 | 0.88 |
| | 2 | 0.12 | 102.9 | 0.02 | ND | ND | 0.23 | 0.03 | 0.08 | 0.56 |
| 25° C./60% RH | 1 | 1.33 | 103.7 | 0.19 | ND | ND | 0.79 | 0.34 | 0.13 | 1.66 |
| | 2 | 0.77 | 103.8 | 0.04 | ND | ND | 0.54 | 0.15 | 0.06 | 0.93 |
| 40° C./75% RH | 1 | 1.76 | 102.5 | 0.05 | ND | ND | 0.46 | 0.09 | 0.25 | 1.17 |
| | 2 | 1.19 | 100.8 | 0.35 | ND | ND | 1.51 | 0.58 | 0.24 | 2.98 |

$; Single unknown impurity;
$$ total impurity

TABLE 3a

Physical stability of the reconstituted solution of the lyophilized cake of example IV

| Stability condition | | Reconstitution | | | | |
|---|---|---|---|---|---|---|
| Temp/humidity | Time in months | Time in Secs | pH | Abs. at 420 nm | % tran. * | Osmolality |
| Initial | | 48 | 7.8 | 0.042 | 99.719 | 296 |
| 2-8° C. | 1 | 20 | 7.9 | 0.13 | 98.123 | 290 |
| | 2 | 22 | 7.8 | 0.017 | 97.992 | 290 |
| 25° C./60% | 1 | 25 | 7.9 | 0.011 | 98.895 | 288 |
| | 2 | 24 | 7.8 | 0.061 | 97.794 | 285 |
| 40° C./75% | 1 | 30 | 7.9 | 0.018 | 97.48 | 284 |
| | 2 | 28 | 7.8 | 0.018 | 97.925 | 271 |

Example V 3.5 mg of Bortezomib having a total impurity of about 0.51%, single maximum unknown impurity of about 0.11%, specific optical rotation of about −53.4°, residual solvent content of less than 100 ppm was taken in a 5 ml vial. Tromethamine (3.31 mg) was weighed and mixed in the vial. Water for injection was added with continuous stirring. The mixture was warmed at 35° C. to 40° C. The mixture was stirred and subjected to bath sonication till clear solution was obtained. Accurately weighed quantity of sodium chloride (30 mg) was added in the vial and dissolved in the solution. The pH of the clear solution was adjusted with 5% hydrochloric acid to 7.0. The volume was made up and then the solution was filtered through 0.2-0.8 micron syringe filter. The clear solution was lyophilized in the vials. The lyophilized cake was stored in vials at various stability conditions and was subjected to the chemical and physical stability. The results of the stability are tabulated below.

TABLE 4

Chemical stability of the lyophilized cake of composition of example V

| Stability condition | | | | Degradation-known and unknown impurities | | | | | | |
|---|---|---|---|---|---|---|---|---|---|---|
| Temp/humidity | Time in months | Water content (KF) | Assay | A | B | D | H | I | $ | $$ |
| Initial | | 0.80 | 102.1 | 0.02 | | nd | 0.08 | 0.02 | 0.23 | 0.57 |
| 2-8° C. | 1 | 0.43 | 101.8 | 0.03 | | Nd | 0.06 | 0.07 | 0.18 | 0.57 |
| 25° C./60% RH | 1 | 0.36 | 100.7 | 0.03 | | Nd | 0.07 | 0.07 | 0.16 | 0.56 |
| 40° C./75% RH | 1 | 0.13 | 98.60 | 0.04 | | Nd | 0.12 | 0.11 | 0.16 | 0.68 |

$; Single unknown impurity;

$$ total impurity;

nd: not detectable

The lyophilized cake in the vials was reconstituted with 3.5 ml of water for injection. The reconstitution was quick and took less than 90 seconds. The final reconstituted solution was clear. This reconstituted solution was stored at 2° C. to 8° C. for a period of 48 hours. The reconstituted solution was also subjected to storage temperatures of 20° C. to 25° C. The stored solution was analyzed for related substances i.e unknown impurities and total impurities and the bortezomib content.

TABLE 5a

Physical stability of the reconstituted solution of the lyophilized cake of example V

| Condition Temp/RH | Period In month | Reconstitution Time in Seconds | pH | Abs. at 420 nm | % tran.* | Osmolality |
|---|---|---|---|---|---|---|
| Initial | 0 | 25 | 6.8 | 0.014 | 98.53 | 289 |
| 2-8° C. | 1 | 22 | 6.8 | 0.013 | 97.72 | 283 |
| 25° C./60% | 1 | 29 | 6.6 | 0.014 | 97.65 | 291 |
| 40° C./75% | 1 | 36 | 6.7 | 0.010 | 97.2 | 291 |

% Transmission;

abs = absorbance

The assay and the impurities were determined by HPLC. The solutions were found to be stable over a period of 48 hours.

TABLE 5b

Chemical stability of the reconstituted solution of the lyophilized cake of example IV filled in vials (V) and syringe (S)

| Time in hours | % Assay | | Related substances (Impurity)-Known impurity | | | | | | | | | | % total impurities | | % single maximum unknown impurity | |
|---|---|---|---|---|---|---|---|---|---|---|---|---|---|---|---|---|
| | | | V | | | | | S | | | | | | | | |
| | V | S | A | B | D | H | I | A | B | D | H | I | V | S | V | S |
| 0 | 99.3 | 99.3 | 0.03 | ND | | 0.07 | 0.07 | 0.03 | ND | | 0.07 | 0.07 | 0.6 | 0.6 | 0.19 | 0.19 |
| 4 | 98.5 | 98.8 | 0.03 | | | 0.07 | 0.08 | 0.03 | | | 0.07 | 0.08 | 0.53 | 0.54 | 0.16 | 0.15 |
| 8 | 97.9 | 96.7 | 0.03 | | | 0.08 | 0.08 | 0.03 | | | 0.08 | 0.08 | 0.53 | 0.54 | 0.16 | 0.19 |
| 12 | 98.3 | 96.4 | 0.04 | | | 0.09 | 0.09 | 0.03 | | | 0.09 | 0.09 | 0.55 | 0.57 | 0.17 | 0.19 |

ND: not detectable

The invention claimed is:

1. A method of preparing a lyophilised composition of N-(2-pyrazine) carbonyl-L-phenylalanine-L-leucine boronic acid, said method consisting of:

(a) dissolving N-(2-pyrazine)carbonyl-L-phenylalanine-L-leucine boronic acid having a total impurity of less than 0.51%, tromethamine and a bulking agent in water, wherein the N-(2-pyrazine) carbonyl-L-phenylalanine-L-leucine boronic acid and tromethamine are present in a molar ratio of at least about 1:3;

(b) adjusting the pH of the solution obtained in step (a) to about 6.8 to 7.2;

(c) subjecting the solution obtained in step (b) to sterilization;

(d) filling the solution obtained in step (c) into vials and lyophilizing the solution.

2. A lyophilized composition obtained by the method of claim 1.

3. The method according to claim 1, wherein the bulking agent is selected from the group consisting of potassium chloride, sodium chloride, lactose, sucrose, maltose, trehalose and mixtures thereof.

\* \* \* \* \*